United States Patent
Childress et al.

(10) Patent No.: US 12,235,236 B2
(45) Date of Patent: Feb. 25, 2025

(54) SENSORS WITH CAPACITIVE TRANSDUCTION VIA METAMATERIALS FOR GAS DETECTION

(71) Applicant: Northeastern University, Boston, MA (US)

(72) Inventors: Anthony Childress, Boston, MA (US); Ahmed Busnaina, Needham, MA (US)

(73) Assignee: Northeastern University, Boston, MA (US)

( * ) Notice: Subject to any disclaimer, the term of this patent is extended or adjusted under 35 U.S.C. 154(b) by 464 days.

(21) Appl. No.: 17/829,221

(22) Filed: May 31, 2022

(65) Prior Publication Data

US 2022/0381730 A1 Dec. 1, 2022

Related U.S. Application Data

(60) Provisional application No. 63/194,358, filed on May 28, 2021.

(51) Int. Cl.
*G01N 27/02* (2006.01)
*G01N 27/416* (2006.01)
*G01N 33/00* (2006.01)
*G01N 33/24* (2006.01)

(52) U.S. Cl.
CPC ..... *G01N 27/4162* (2013.01); *G01N 33/0021* (2013.01); *G01N 33/24* (2013.01)

(58) Field of Classification Search
CPC ........... G01N 27/4162; G01N 33/0021; G01N 33/24; G01N 21/64; G01N 27/02; G01N 27/027; G01N 2027/222; G01N 27/227; G01J 3/44

See application file for complete search history.

(56) References Cited

U.S. PATENT DOCUMENTS

| | | | |
|---|---|---|---|
| 8,573,030 B2 * | 11/2013 | Gole | G01N 27/127 73/1.01 |
| 2012/0118751 A1 * | 5/2012 | Cai | G01N 33/54346 977/773 |
| 2012/0327417 A1 * | 12/2012 | Amako | B82Y 20/00 977/773 |
| 2014/0036263 A1 * | 2/2014 | Kim | G01N 21/658 422/69 |
| 2014/0211196 A1 * | 7/2014 | Samuels | G01J 3/0205 356/244 |

FOREIGN PATENT DOCUMENTS

| | | | | |
|---|---|---|---|---|
| CN | 101443656 A | * | 5/2009 | ............. G01N 27/22 |
| JP | 2014190911 A | * | 10/2014 | |

* cited by examiner

*Primary Examiner* — Abdullahi Nur
(74) *Attorney, Agent, or Firm* — Verrill Dana, LLP

(57) ABSTRACT

Devices and methods for detecting an analyte in a gas involve the use of plasmonic excitation of a nanostructured sensing element that is tuned to absorb at a narrow bandwidth specific for light absorbed by the analyte. The sensing element can be used as a capacitive or inductive element in a circuit.

22 Claims, 8 Drawing Sheets

Grid

- Principle: NIR resonance cavity
- 1-1.4 μm pitch, 400 nm depth

Nano-pillar array
- Principle: Plasmonic resonance
- 500 nm pitch, 400 nm height

SENSORS WITH CAPACITIVE TRANSDUCTION VIA METAMATERIALS FOR GAS DETECTION

CROSS-REFERENCE TO RELATED APPLICATIONS

This application claims priority to U.S. Provisional Application No. 63/194,358, filed 28 May 2021, which is incorporated herein by reference in its entirety.

BACKGROUND

Gas detectors have become of greater significance for protecting public safety, and are used for a wide range of applications in industrial plants, refineries, pharmaceutical manufacturing, fumigation facilities, paper pulp mills, public transport areas, hazmat operations, waste-water treatment facilities, vehicles, indoor air quality testing, and homes. Gas detectors can be used, for example, to detect flammable or toxic gases as well as oxygen depletion in an environment. Common gas detector technologies include flame gas sensors, photoionization detectors, infrared point sensors, ultrasonic sensors, catalytic or electrochemical gas sensors, and metal-oxide-semiconductor sensors (MOS sensors). Further gas detectors that are readily deployable in a variety of environments are needed for widespread monitoring purposes.

SUMMARY

The technology described herein provides devices and methods for detecting gas molecules through the use of plasmonic modes in a nanostructured sensing element. The sensing element includes a nanostructure array that is tuned such that a local field established by plasmonic modes of the nanostructure array affects the capacitance or inductance of the sensing element, which is detected by a circuit in the sensor device. Light incident upon the sensing element can be absorbed by an analyte present in a sample gas, leading to alteration of the capacitance or inductance of the sensor element. A light source within the device illuminates a flow path for the sample gas, and the nanostructure array is tuned to an electromagnetic radiation wavelength band that encompasses an absorbance wavelength band of the analyte. The preferred electromagnetic radiation wavelength band is that of the near infrared (NIR), which is the wavelength range from about 780 nm to about 2500 nm.

One aspect of the present technology is a sensor device for gas detection; the device includes a housing configured with a flow path for a sample gas through the housing, a light source disposed within the housing to direct light across the flow path, and a sensing element disposed within the housing to receive light emitted by the light source and crossing the flow path or a portion thereof. The light source emits light containing an emission wavelength band overlapping with an absorbance spectrum or portion thereof of a first gas analyte selected for detection. The sensing element contains a nanostructure array formed of conductive nanostructures attached to a substrate and encapsulated in a dielectric material. The nanostructure array and the dielectric material are tuned to provide plasmonic absorption by the conductive nanoelements over an absorbance wavelength band that overlaps with the absorbance spectrum or a portion thereof of the first analyte, such that a local field established by plasmonic modes of the nanostructure array affects a capacitance or inductance of the sensor device.

Another aspect of the technology is a method of detecting the presence of a first selected analyte. The method includes the steps of providing the sensor device described above, establishing a baseline capacitance or inductance of the sensing element when no analyte is present in the flow path, detecting a change in the capacitance or inductance when the first analyte is present in the flow path, and transmitting a signal representative of the change in capacitance or inductance to electronic circuitry and/or a processor, and/or a receiver. In an embodiment, the method further includes the steps of providing a second sensor element tuned to absorb at an absorbance wavelength band of a second analyte for detection (different from that of the first analyte); detecting a change in capacitance or inductance when the second analyte is present in the flow path, and transmitting a signal representative of the change in the capacitance or inductance to electronic circuitry, and/or a processor, and/or a receiver.

Yet another aspect of the technology is a system for gas detection. The system includes the sensor device described above, a pump and/or an inlet operative to transport a gas sample suspected of comprising the first analyte through the flow path, and a processor operative to detect a change in capacitance or inductance of the sensor element when the first analyte is present in the flow path and optionally to transmit information indicative of detection of the first analyte to a receiver or over a network.

The present technology can be further summarized by the following list of features.

1. A sensor device for gas detection; the device comprising:
    a housing configured with a flow path for a sample gas through the housing;
    a light source disposed within the housing to direct light across the flow path, the light source emitting light comprising an emission wavelength band overlapping with an absorbance spectrum or portion thereof of a first analyte selected for detection;
    a sensing element disposed within the housing to receive light emitted by the light source and crossing the flow path or a portion thereof, the sensing element comprising a nanostructure array of conductive nanoelements attached to a substrate and encapsulated in a dielectric material, wherein the nanostructure array and the dielectric material are tuned to provide plasmonic absorption by the conductive nanoelements over an absorbance wavelength band that overlaps with the absorbance spectrum or a portion thereof of the first analyte, such that a local field established by plasmonic modes of the nanostructure array affects a capacitance or inductance of the sensor device.
2. The device of feature 1, wherein the sensing element comprises a capacitive element, and the nanostructure array encapsulated in the dielectric material is disposed between opposed conductive surfaces of the capacitive element.
3. The device of feature 1 or 2, wherein the nanostructure array comprises nanoscale pillars, rods, or tubes having a spherical or polyhedral cross-sectional shape.
4. The device of any of the preceding features, wherein the sensing element is connected with an electronic circuit capable of producing a signal in response to a change in capacitance or inductance of the sensing element.
5. The device of any of the preceding features, further comprising a second sensor element tuned to detect a presence of a second analyte selected for detection, the second analyte having an absorbance wavelength band different from that of the first analyte.

6. The device of any of the preceding features, wherein the light source emits light over an emission wavelength band in the range from about 700 nm to about 2500 nm.

7. The device of any of the preceding features, wherein the dielectric material comprises polyethylene, polypropylene, polytetrafluoroethylene, polyethylene terephthalate, polycarbonate, poly(methyl methacrylate), polystyrene, polyimide, bisbenzocyclobutene resin, polyvinylidene chloride, titanium dioxide, strontium titanate, barium strontium titanate, barium titanate, calcium copper titanate, or a combination thereof.

8. The device of any of the preceding features, wherein the nanostructure array comprises nanostructures with a height of about 400 nm.

9. The device of any of the preceding features, wherein the nanostructure array comprises nanostructures with a diameter in the range from about 100 nm to about 250 nm.

10. The device of any of the preceding features, wherein the nanostructure array comprises a plurality of periodically arranged apertures with a diameter of about 1 μm and a wall between adjacent apertures having a thickness of about 200 nm.

11. The device of any of the preceding features, wherein the nanostructure array comprises nanostructures comprising silver, gold, platinum, copper, or a combination thereof.

12. A method of detecting a presence of a first selected analyte, the method comprising the steps of:
    (a) providing the sensor device of feature 1;
    (b) establishing a baseline capacitance or inductance when no analyte is present in the flow path;
    (c) detecting a change in the capacitance or inductance when the first selected analyte is present in the flow path; and
    (d) transmitting a signal representative of the change in the capacitance or inductance to electronic circuitry and/or a processor.

13. The method of feature 12, wherein the first selected analyte is selected from the group consisting of hydrogen, ammonia, hydrogen sulfide, hydrogen fluoride, and hydrocarbons.

14. The method of feature 12 or 13, wherein the first selected analyte is a hydrocarbon selected from the group consisting of methane, ethane, propane, and butane.

15. The method of any of features 12-14, further comprising the steps of:
    (c1) providing a second sensor element tuned to absorb at an absorbance wavelength band of a second analyte for detection;
    (c2) detecting a change in capacitance or inductance when the second analyte is present in the flow path; and
    (c3) transmitting a signal representative of the change in the capacitance or inductance to electronic circuitry or a processor.

16. The method of feature 15, wherein the first analyte is a hydrocarbon and the second analyte is a hydrocarbon different from the first analyte.

17. The method of feature 15, wherein the second analyte is water vapor.

18. A system for gas detection; the system comprising: the sensor device of feature 1;
    a pump and/or an inlet operative to transport a gas sample suspected of comprising the first analyte through the flow path; and
    a processor operative to detect a change in capacitance or inductance of the sensor element when the first analyte is present in the flow path and to transmit information indicative of detection of the first analyte to a receiver or over a network.

19. The system of feature 18 comprising two or more sensor devices of feature 1, each of the two or more sensor devices operative to detect a different analyte present in the flow path.

20. The system of feature 19 configured to detect methane and a different hydrocarbon or methane and water vapor.

21. The system of any of features 18-20, further comprising a mass flow meter operative to provide a measured flow of the sample analyte to the processor.

22. The system of any of features 18-21 that is configured for deployment in an oil or gas rig, refinery, analytical lab, manufacturing facility, public transport area, flammable liquid or gas cylinder storage or distribution facility, vehicle, outdoor hazmat area, hazardous materials area, or residence.

As used herein, the term "nanoscale" refers to structures having at least one dimension in the range from about 1 nm to about 999 nm, and the term "microscale" refers to structures having at least one dimension in the range from about 1 μm to about 999 μm.

As used herein, the term "about" refers to a range of within plus or minus 10%, 5%, 1%, or 0.5% of the stated value.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with the alternative expression "consisting of" or "consisting essentially of".

DETAILED DESCRIPTION

The technology described herein provides methods and devices for detecting analytes through the use of plasmonic excitations. A plasmonic sensing element is used to detect an analyte. The sensing element includes a nanoscale absorber that is tuned to absorb at a narrow bandwidth for use as a capacitive and/or an inductive element in a circuit. A light source that is incident upon the sensing element causes a change in capacitance or inductance due to the absorbance of light by an analyte present in a gas stream.

Figure 1A:
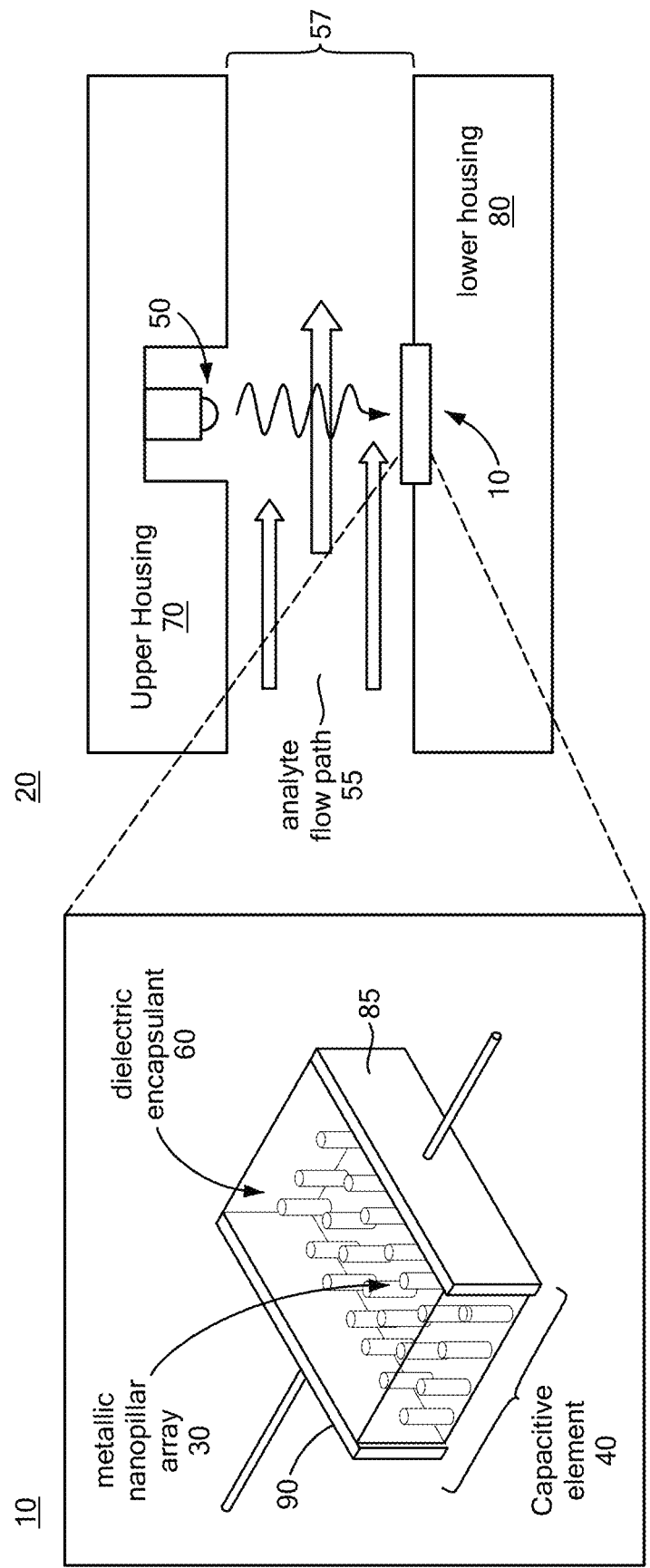
FIG. 1A is a schematic illustration of a gas sensor of the present technology. A cross sectional view is shown on the right, and detail of the capacitive sensor element is shown on the left. Gas molecules in analyte flow path 55 absorb NIR radiation, causing a change in field strength which is detected by capacitive element 40, which includes nanopillar array 30 encapsulated by dielectric medium 60.
Figure 1B:
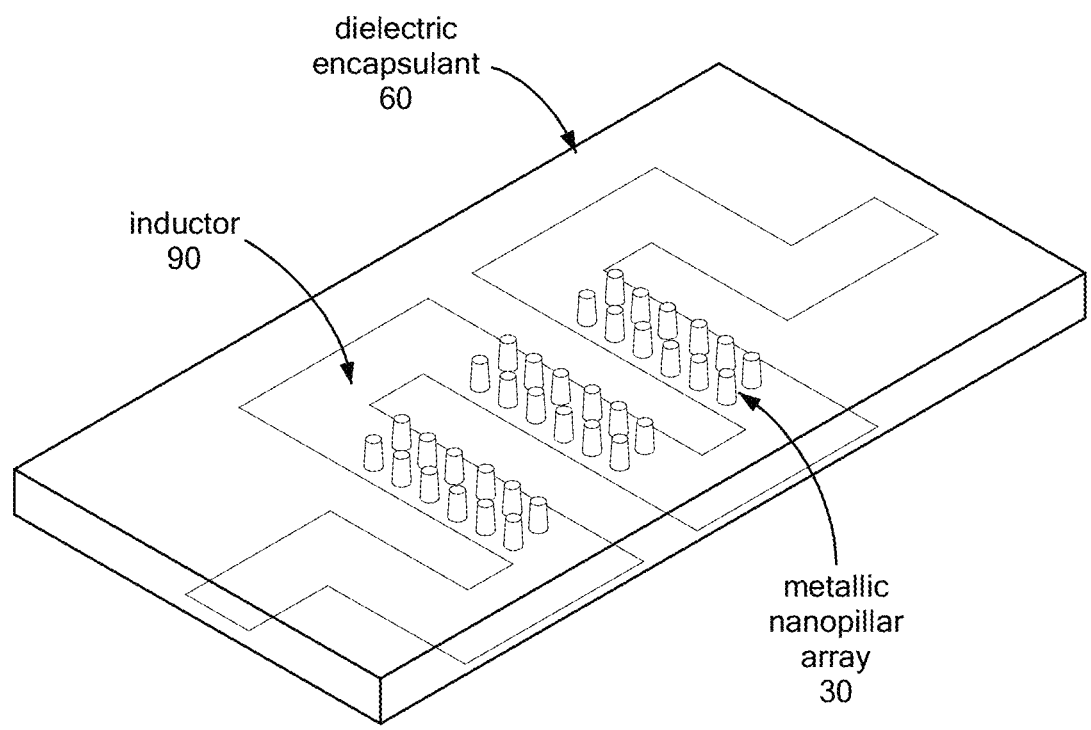
FIG. 1B is a schematic representation of an inductive sensor element. Inductor element 90, a conductive pathway having a form that provides an induction effect, contains aligned arrays of conductive nanorods 30 at positions that allow the nanorods to modulate the induction effect through plasmonic absorption of NIR radiation, which alters the electric field sensed by the inductor, allowing the inductor to be used as a gas analyte sensor. The sensor element can include a dielectric encapsulant 60, to improve and tune the response of the nanorods.

FIG. 1A (right side) shows a cross section of sensor unit 20. Light source 50 focuses light through analyte flow path 55 onto sensing element 10. Upper housing 70 and lower housing 80 are separated to create a flow path having length 57; the flow path accommodates a sample gas which is suspected of containing a selected analyte. An enlarged view of sensing element 10 (FIG. 1A, left side) shows capacitive element 40. The sensing element includes a sensing array, which in the depicted embodiment is an array of metallic nanopillars 30 that is encapsulated by dielectric encapsulant 60. Capacitive surfaces 85 and 90 measure changes in the dielectric properties of the encapsulated nanopillar array which is present between them. Gas molecules present in the analyte flow path absorb NIR radiation, causing a change in field strength sensed by the sensing element, whose plasmonic absorption is tuned to an absorbance bandwidth that overlaps with all or a selected portion of the absorbance spectrum of the intended analyte and is selective or specific for the analyte. The change in capacitance is detected by a detection circuit (not shown) of the device, which change in capacitance signals the presence and/or concentration of analyte present in the sample gas. Further electronic circuitry can transmit a signal representative of a change in the capacitance or inductance to a processor within the device (not shown) or to an external receiver. The circuitry or processor can be configured, for example, to send an alarm or to transmit a measurement. The device depicted in FIG. 1A can be used in a method of selective analyte detection by virtue of the selected absorbance band of the sensing element.

Figure 1C:
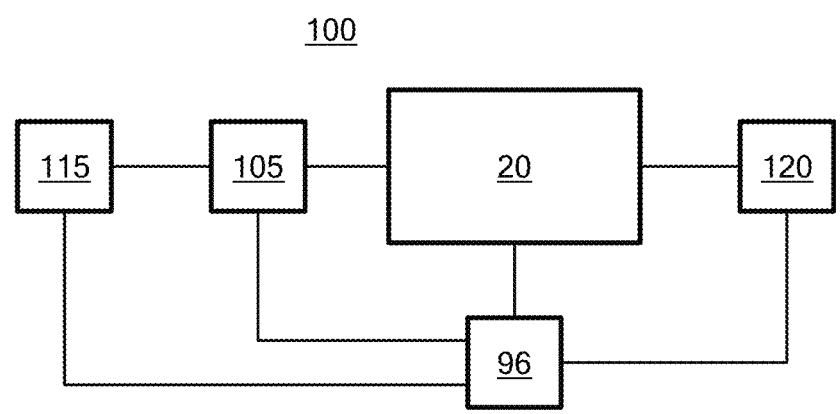
FIG. 1C shows a schematic of a deployable system 100 for gas detection including the sensor unit of FIG. 1A and optional features for processing/measuring the analyte flow path 55 in various environments.

FIG. 1C shows an embodiment of a system 100 for gas detection. The system includes sensor unit 20 of FIG. 1A with induction pump 105 or vacuum pump 120 to provide gas flow, and optional mass flow controller or mass flow meter 115 to control and/or monitor flow. In this embodiment, processor 96 is in communication with the pumps and optional mass flow control/meter 115. Optional additional unit(s) (not shown) can be additional sensor units or a functionalized area for sampling and/or processing in specific diverse environments, such as a gas orifice, filter, or dryer. A network of such deployable systems can be utilized for detection of a variety of gases in an environment. In one configuration, each of the deployable systems can be configured for detection of a different gas. In another configuration, each of the deployable systems is configured for detection of the same gas, and each is deployed at a distinct location within an environment, so as to monitor the analyte gas at specific locations of the environment over time.

The present technology has advantages over other detectors which rely on a shift of absorbance peaks due to the change of the refractive index in the environment caused by the presence of gas molecules. This, in turn, requires the use of a photodetector and monochromators to determine the absorbance spectra. The technology described herein does not rely on the use of these, but instead utilizes the narrow bandwidth of a nanostructured plasmonic sensor.

The sensor array described herein can be implemented as a circuit element and can leverage the local field enhancement of plasmonic structures to modulate an electronic signal, resulting in direct electronic transduction as opposed to a photoelectric method of transduction. In the present sensor element, the plasmonic modes of the nanostructures serve to couple the optical signal to an electronic signal.

The nanostructure used in the sensor array can be tailored such that its plasmonic modes are excited by a certain frequency that coincides with a portion of an absorbance spectrum, such as a wavelength band centered on an absorbance peak, of the desired analyte. An LED, diode laser, or other light source 50 capable of emitting over a wavelength band overlapping with the absorbance spectrum of the analyte or a portion thereof can be used to illuminate the flow path covering the sensing element. The pathlength is shown as 57 in FIG. 1A. The light can be focused on the sensing array using a lens or other suitable optical elements in order to maximize the strength of the signal. In the absence of an analyte, the incident light provides a baseline signal which can be used as a reference for detection of the analyte. Within the nanostructured sensor array, the local field established by the plasmonic modes affects the capacitance of the circuit element containing the sensor array. This change in capacitance is monitored and serves as a signal for detection of the analyte gas in the flowing sample gas. When the gas molecules pass between the light source and the sensing array, they absorb a portion of the incident light. This causes a modulation of the plasmon intensity on the sensing element and thus a change in the measured capacitance or inductance; the sensing circuit can be configured to detect a change in either capacitance or inductance. The sensor can be made specific to a particular gas through tailoring the sensor array geometry to absorb within a narrow bandwidth centered at the analyte's peak absorbance; thus, there is no need for additional optical filters or monochromators to process the signal. It is well known to the skilled practitioner how to select the material, shape, height and width of the nanostructures, as well as their separation and pattern of arrangement in the array, as well as the dielectric material of the encapsulant and its dielectric properties, so as to provide a suitable plasmonic absorption band for detection of the desired analyte. Using the pathlength or distance 57, the sensor unit can provide quantitative data for an analyte, i.e., a quantitative measure of the concentration of the selected analyte in the sample gas can be determined.

Examples of plasmonic structures that may be used as the absorbing element include arrays containing conductive nanostructures such as nanopillars, a monolayer of nanoparticles of various shapes (spheres, rods, polyhedrons), nanoparticles of various shapes suspended within a medium, a mesh structure containing periodic voids to create a plasmonic effect, and a grating or series of gratings containing parallel grooves in a material. Other electronic parameters such as inductance may also be used for measurement if a suitable sensor array is implemented as an inductive circuit element. For the case of inductance, the absorbing element would be placed on top of the inductive circuit. When there is a change in absorbance due to the presence of analyte, the electric field in the vicinity of the inductor will change, yielding a measurable change in inductance.

The absorption bandwidth of the plasmonic sensor is highly sensitive to the dielectric function of both the conductive nanostructure and its surroundings and can range from 30-60 nm for a well-formed array of pillars. This variability can be detrimental where the plasmonic structure is tailored to absorb at a particular frequency that is required to remain constant. This aspect can be accounted for by encapsulating (or partially encapsulating) the plasmonic structure within a dielectric of known properties through which sample material including analytes cannot penetrate. This ensures that the dielectric environment of the plasmonic structure can remain constant.

Capacitance is determined in part by the dielectric function of the material that is present surrounding the conductive nanostructure surfaces. When a potential is applied between the conductive surfaces of the sensor element (structures 85 and 90 of FIG. 1A), the polarization of the dielectric material serves to store electromagnetic energy. In the present technology, the sensor array and dielectric encapsulant are the materials disposed between two conductive surfaces or plates. The enhancement of the electric field of the sensor array due to the plasmonic response can, in turn, affect the polarizability of the dielectric medium, leading to a measurable change in capacitance when the local field is modulated by a change in incident light intensity of suitable wavelength.

The present technology provides a number of advantages. For example, the technology does not rely on photodetectors. The technology also does not rely on the shift of plasmonic frequency. Operation depends on a narrow bandwidth of plasmonic absorption, which can be adjusted by adjusting the material, geometry, and/or distribution of nanoelements in the plasmonic absorber. The technology functions by altering the polarizability of a dielectric medium, which in turn affects the capacitance or inductance of the sensor array as a circuit element. The technology does not require optical filters, prisms, or monochromators.

The present technology does not rely on expensive components such as monochromators, and utilizes a sensor that can be fabricated at low cost by nanoprinting methods, and therefore is much less costly than previously available technology. The present technology also does not rely on measuring a shift of plasmonic frequency. The sensing element can be encapsulated in a dielectric material, thereby protecting it from moisture, oxidation, and poisoning by reactive gases or other environmental factors. The sensing element can be made specific for any of a wide range of gases through tuning the plasmonic properties of the sensor. The technology utilizes a simple design that does not require moving parts or pattern liftoff for fabrication. The technology can allow monitoring to be done by a compact, robust sensor that can be mass produced and distributed over large areas due to its low cost.

The present technology has a number of applications. For example, the technology can be used for the detection of gas molecules that are difficult to detect via chemical means. The technology can be used for the monitoring of gas leaks. Monitoring can be performed at low cost. The technology can be used for the detection of gases that could harm traditional catalyst-type gas detectors. The technology can be used in military applications and civil aviation.

The present gas sensor can utilize narrow band infrared plasmonic absorption of printed micro and nanostructures. Technology to print such nanostructures in a scalable fashion can be used. Methods of fabricating nanostructures with electric field directed assembly of nanoelements, and nanostructures fabricated by nanoelement assembly are described in WO 2014/005147A2, "Three-Dimensional Crystalline, Homogeneous, and Hybrid Nanostructures Fabricated by Electric Field Directed Assembly of Nanoelements," which is hereby incorporated by reference in its entirety. Other lithography techniques such as atomic layer or chemical vapor deposition also can be used.

Using these methods, nanoscale grids and pillars can be printed in patterns that allow for a tailored narrow-band absorbance spectrum in the near infrared (NIR) region. The nanostructures can be positioned such that the electric fields generated from incident NIR radiation can affect the measured capacitance of a circuit element that serves as the sensor. The absorbance band of the nanostructured sensor can be tuned to coincide with the absorption spectrum of a specific gas. Thus, when the gas molecules pass along the device sample flow path and through the emitted light of the light source, a change in the absorption at the sensor element produces a change in capacitance in the sensor circuit, allowing the analyte gas concentration to be monitored over time. These devices can be robust to moisture, temperature extremes, and gases that could poison or corrode traditional catalysts used to detect certain gases such as methane. The gas sensing device can be adapted to measure a variety of gases by tailoring the absorbance spectrum of the nanostructured sensor. Examples of analyte gases include various hydrocarbons, including methane, ethane, propane, and butane, as well as hydrogen, ammonia, and hydrogen sulfide. If a gas molecule has a sharp absorbance in the near infrared range, then it can be detected by the means described here. As used herein, the term "hydrocarbon" refers to compounds including carbon and hydrogen. Hydrocarbons can be generally invisible to the human eye, may only have weak odors, and can have diverse molecular structures. For example, mercaptan is often added to natural gas (which can be a mixture of methane and other hydrocarbons) to provide an alarm odor. By tailoring the absorbance spectrum of the nanostructured sensor, the device can be applied to measure any gas including a non-hydrocarbon and/or a hydrocarbon and various substituents on the hydrocarbon (i.e., elements in addition to carbon and hydrogen). The devices and methods can be utilized in a hazardous area, which is an area in which the atmosphere contains, or may contain in sufficient quantities to be hazardous, flammable or explosive gases or vapors.

Methane is a gas that is difficult to detect without the use of expensive equipment, and it can be used here as an example of an application of the technology. The detection of methane is critical for the proper treatment and storage of natural gas, or when working in any environment where natural gas may be present. Its detection is also important for studies of climate change. Methane has no functional groups, and so is rather unreactive, making its detection via chemical means difficult. Typical methods for detecting methane include heated catalysts and infrared detection. A heated catalyst bed requires high temperatures, a large volume, and is susceptible to catalyst poisoning by sulfates that may be present in the atmosphere. A more reliable method for detecting methane is to use a light source that emits in the near infrared spectrum, typically a diode laser, and a spectrometer packaged together in a single device. Such detectors that rely directly on the absorbance of the analyte are effective but tend to be relatively expensive and large. The device described herein can rely indirectly on the absorbance of the analyte, using a change in absorbance to modulate the capacitance of a plasmonic sensing array. The sensor array can be fabricated with scalable printing methods and as such can result in lower costs. The sensor array can be part of an integrated circuit that will also allow for data transmission.

Figure 2A:
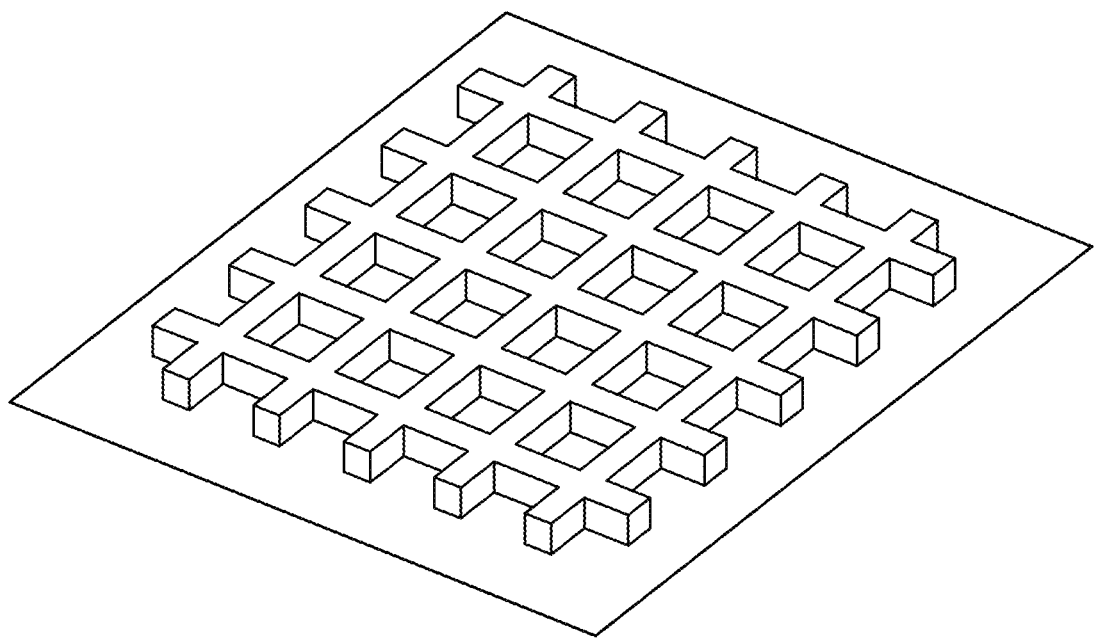
FIG. 2A is a diagram of a nanostructured grid absorber showing example pitch and depth.
Figure 2B:
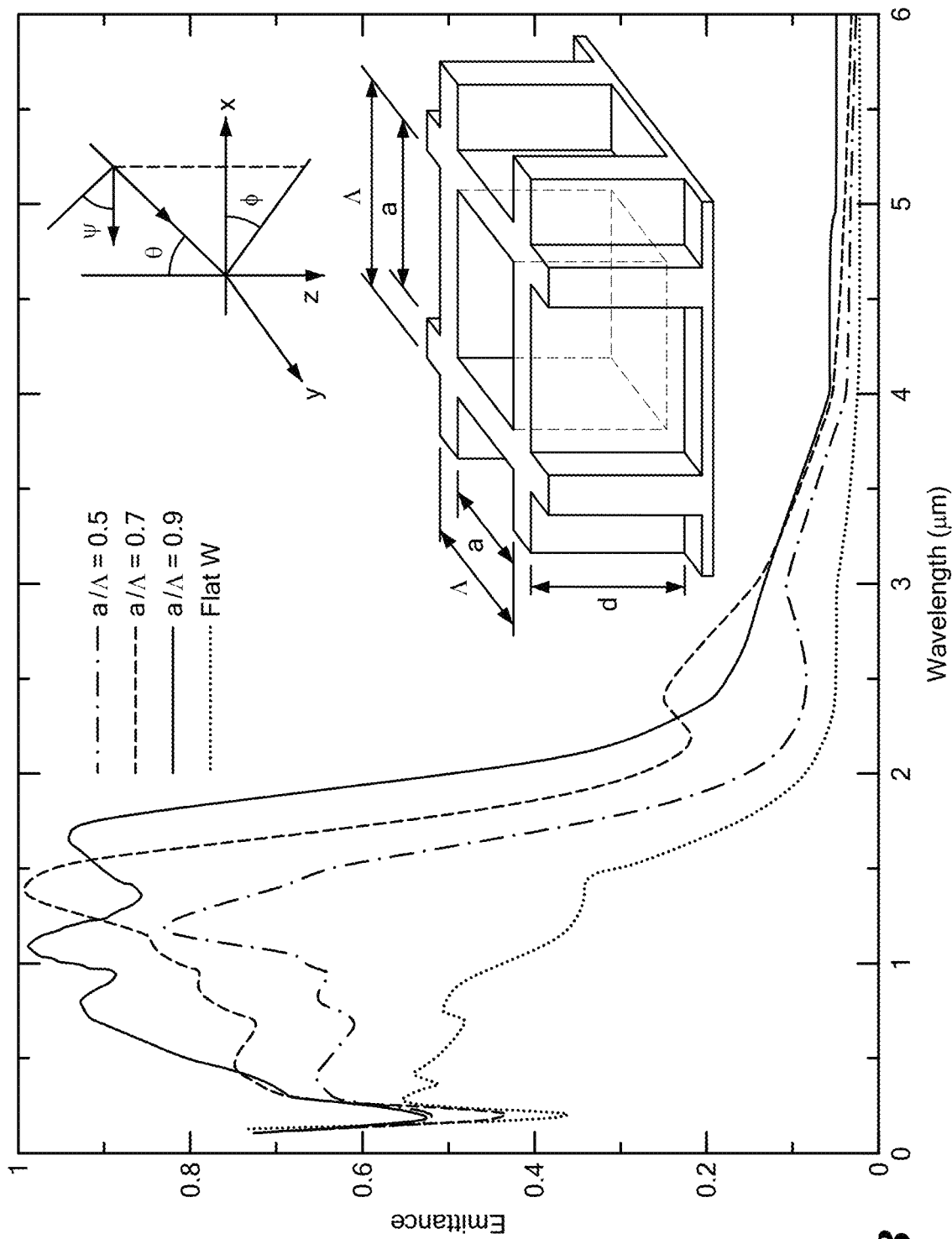
FIG. 2B is a diagram of a nanostructured grid absorber with calculations of the emittance as a function of grid parameters (Sai, et al., 2003).

There are a wide variety of nanostructures available that can be tuned to absorb light of certain wavelengths. These include antennas, sub-wavelength voids in dielectric media, monolayers or suspensions of nanoparticles, and thin dielectric films between metal layers. These can all be fabricated using typical lithography, liftoff, and CVD methods. In addition to these, two examples of nanostructures that are amenable to self-assembly methods are grids and arrays of nanostructures forming pillars, both of which can be used in the device. The concept of controlling the absorbance spectra via nanoscale grid patterns was implemented for use with thermal photovoltaic cells (Heinzel, et al., *AIP Conf. Proc.*, American Institute of Physics, 1999, pp. 191-196, which is hereby incorporated by reference in its entirety). For grids, control of the absorbance spectrum is based on the optical resonance characteristics of a cavity, similar to a waveguide or resonance cavity that is used to direct microwaves. For this reason, a nanostructured grid wherein the cavities are similar in dimension to the desired emission wavelength can be used as the resonance feature. The size and spacing of the grating apertures can be used to tune the absorbance to a narrow band in the NIR, thereby increasing the absorbance in the desired region. Using the rigorous coupled wave analysis method, the absorbance spectrum can be calculated as a function of the size, depth, and periodicity of the apertures as illustrated in the embodiment shown in FIG. 2A. FIG. 2B shows an example of calculations made by varying the aperture/periodicity ratio as found in Sai, et al., *Appl. Phys. Lett.* 82, 1685 (2003), which is hereby incorporated by reference in its entirety. For the NIR range, the aperture would be about 1 µm with a periodicity of about 1.2 µm, meaning the wall between apertures is about 200 nm thick. Using this method, the absorbance and emissivity can be enhanced to near unity for the intended NIR band.

Figure 2C:
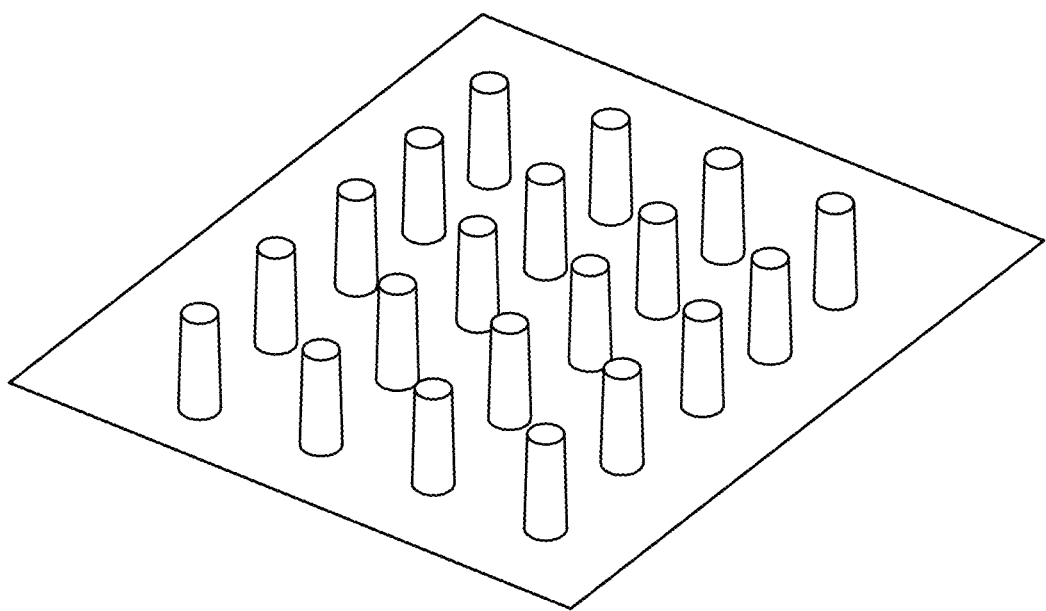
FIG. 2C shows an array of nanopillars for plasmonic control of absorbance.
Figure 2D:
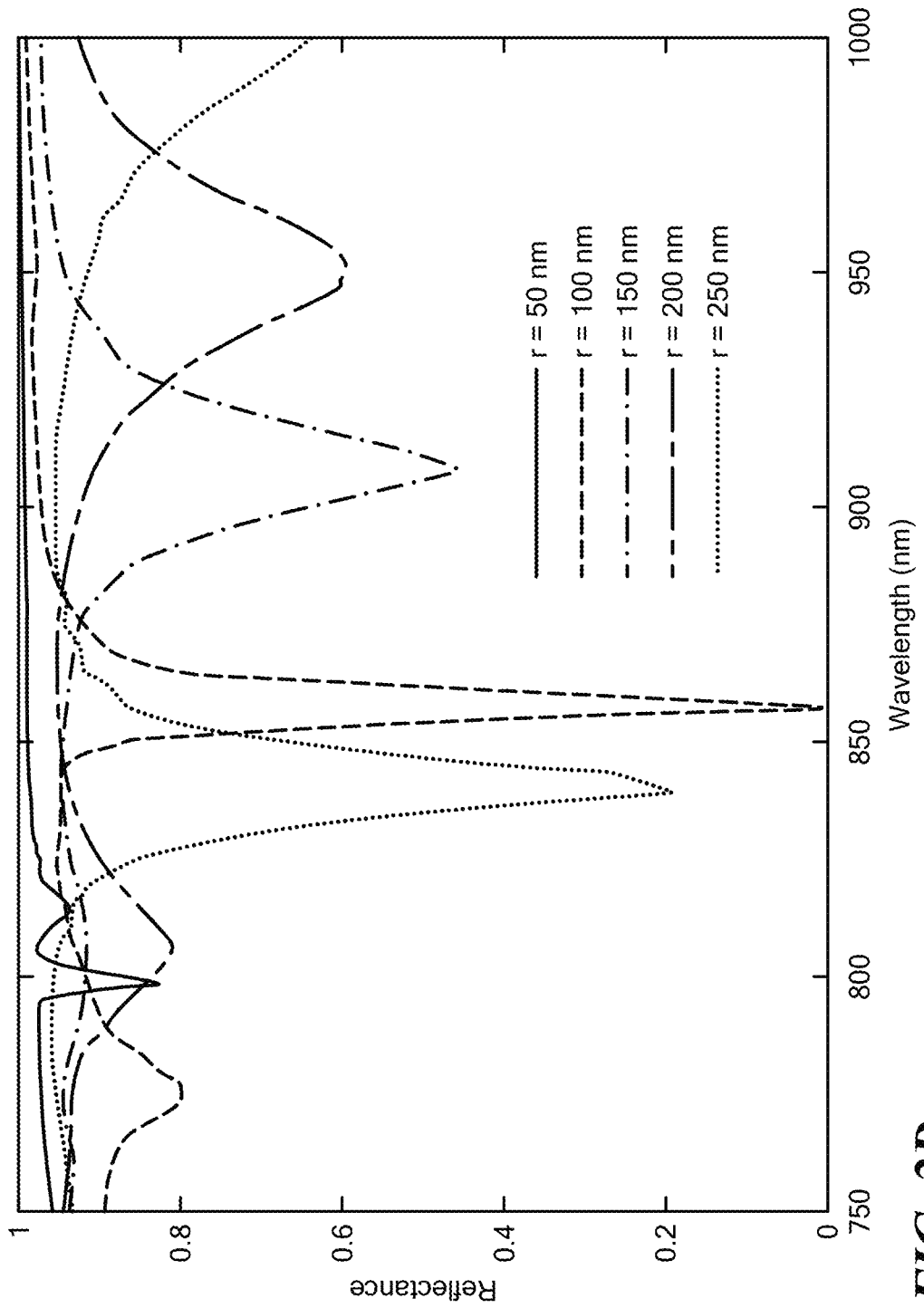
FIG. 2D is a plot of data showing calculated reflectance of nanopillar arrays 400 nm in height with various radii (Cetin, et al., 2011).

The principle of tuning the absorbance and emission band via nanostructures can also be accomplished by the plasmonic response of arrays of metallic pillars. This plasmonic effect is created when incident light causes oscillations of free electrons in the pillars, creating electric fields that couple between pillars and thereby greatly increase absorbance. The plasmonic resonance also results in an intense enhancement of the electric field along the edges of the pillars. Several plasmonic-based photodetectors have been demonstrated in the literature that rely on traditional lithography and CVD deposition methods for fabrication (Senanayake, et al., 2011; Senanayake, et al., *Appl. Phys. Lett.* 97, (2010); Nesser, et al., *Mater. Today Nano* 4, 38, (2018). Using self-assembly methods, plasmonic nanopillar arrays can be fabricated, as shown in FIG. 2C and FIG. 2D (cetin, et al., *Appl. Phys. Lett.* 98, 111110 (2011); Yilmaz, et al., *ACS Nano* 8, 4547 (2014). In the examples of FIG. 2C and FIG. 2D, the peak absorbance wavelength of the array is tuned by adjusting the height, diameter, and pitch of the gold nanoparticle pillars. It is found that a height of 400 nm is optimum with regards to absorbance in the NIR, with increased height leading to less absorbance and a broadening absorbance band. The diameter of the pillars correlates with a redshift of the absorbance, where diameters of 100-250 show a strong response in the NIR (FIG. 2D).

Figure 3A:
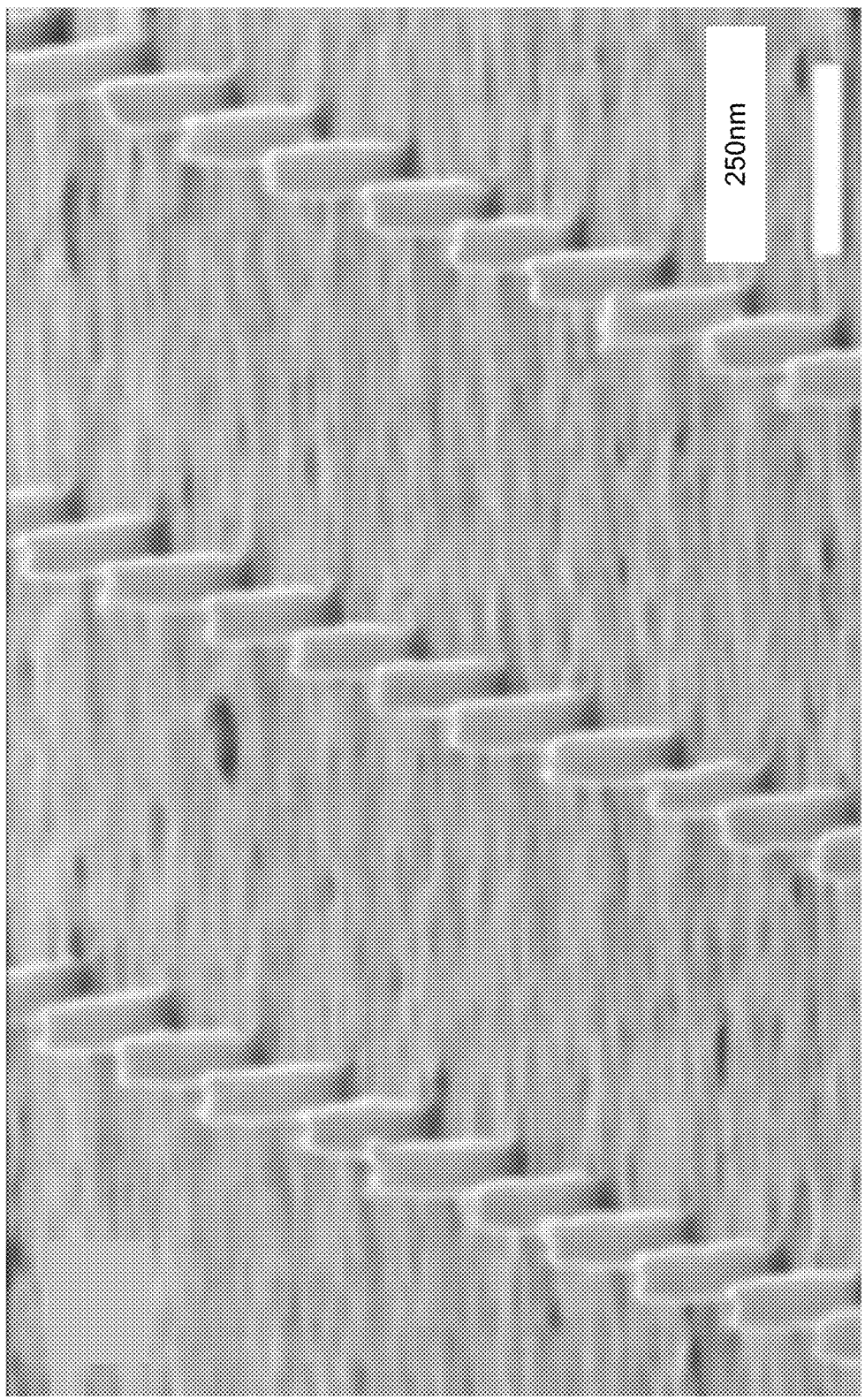
FIG. 3A (Yilmaz, et al., 2014) shows an optical microscopy image of nanopillar arrays fabricated over a 1×1 mm area. The nanopillar arrays are assembled from 20 nm gold nanoparticles.
Figure 3B:
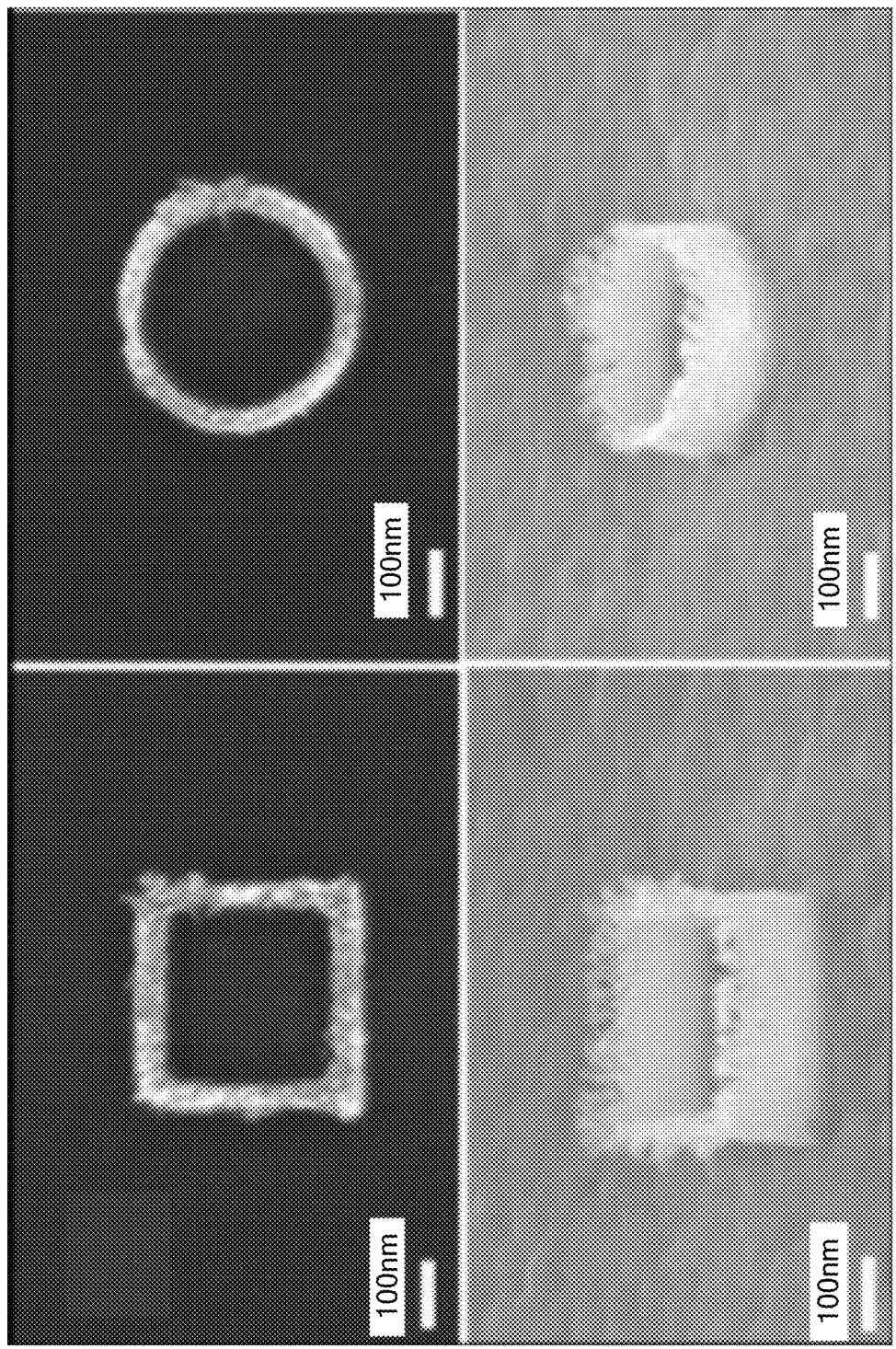
FIG. 3B (Yilmaz, et al., 2014) illustrates examples of nanostructures assembled by CHN such as boxes and rings assembled via dielectrophoretic assembly of gold nanoparticles.

This sensor described herein can be fabricated through scalable methods for printing nanomaterials. Several methods can be used for large scale printing of the nanostructured absorbers detailed above. The methods include electrophoresis and dielectrophoresis where DC and AC currents are used to assemble nanoparticles within vias. Fluidic and convective assembly methods that rely on capillary forces for the assembly of nanoparticles may be used in the case of insulating substrates. FIG. 3A shows assembled nanopillar arrays, while FIG. 3B illustrates that shapes of arbitrary design can also be achieved, which can prove useful for assembling nanoscale grid emitters. The assembly process is lift-off free, low cost, does not require vacuum, and is simpler than traditional microfabrication methods. Methods of fabricating nanostructures of electric field directed assembly of nanoelements and nanostructures fabricated by nanoelement assembly are described in WO 2014/005147, "Three-Dimensional Crystalline, Homogeneous, and Hybrid Nanostructures Fabricated by Electric Field Directed Assembly of Nanoelements," which is incorporated by reference herein in its entirety.

The nanostructured sensor can be incorporated as a capacitive circuit element. This can be accomplished by positioning the sensor array between conductive surfaces that act as capacitive plates and encapsulating the sensor array in a polymer of well-characterized refractive index that has minimal IR absorbance around the desired band. This design can be implemented in a planar (FIG. 1A) or sandwich geometry. In the case of sandwiching the array in a vertical fashion, one of the conductive surfaces can be largely transparent to the incident NIR source. An LED or diode laser may be used as a source of excitation that is incident upon the sensing array. When gas molecules pass between the light source and the sensing array, the absorption lowers the amount of NIR light incident on the sensor, thus reducing the field intensity between the capacitive plates and thereby altering capacitance. The choice of polymer encapsulant is selected based on the dielectric constant of the medium surrounding the pillars or grid, which influences the absorbance spectrum.

While air surrounding conductive nanostructures such as nanorods serves as a dielectric medium, addition of a dielectric material provides consistent performance and protects the nanostructures. Therefore, it is preferred to embed the nanostructures in a fixed and homogeneous dielectric material. Examples of polymers that can conveniently be applied and serve as the dielectric material are bisbenzocyclobutene electronic resin derived from the monomer bisbenzocyclobutene (Senanayake, et al., 2011), polyvinylidene chloride or polyvinylidene dichloride, polyethylene terephthalate, polycarbonate, poly(methyl methacrylate), polytetrafluoroethylene, polypropylene, polyethylene, and chloroprene polymers. Other examples of suitable dielectric materials are polyethylene, polypropylene, polytetrafluoroethylene, polyethylene terephthalate, polycarbonate, poly(methyl methacrylate), polystyrene, polyimide, bisbenzocyclobutene resin, polyvinylidene chloride, titanium dioxide, strontium titanate, barium strontium titanate, barium titanate, and calcium copper titanate. Dielectric materials can be applied by known methods such as spin coating. Alternatively, a negative photoresist can be used as the dielectric material, the vias to form nanostructures patterned by electron beam lithography or photolithography and solvent removal to create the vias, followed by assembly of nanoparticles or other nanoelements in the vias, such as by electrophoresis, dielectrophoresis, flow-mediated assembly, or other known methods.

The required size of the sensor array and the best choice of an encapsulant can be determined via modeling. The required incident NIR light can be provided by an LED. The LED can have an emission center wavelength in the range from about 700 nm to about 3000 nm or in the range from about 750 nm to about 2500 nm. For detecting methane, the incident light can be chosen as 1650 nm, as this corresponds to a major absorbance band of methane and is about 6061 $cm^{-1}$ in the NIR wavelength region.

The sensor architecture does not need to be limited to nanopillars and grids, but can also include other plasmonic structures, as mentioned previously. The nanostructures used in the sensing array can be made from a variety of conductive metal materials such as silver, gold, platinum, copper or conductive polymers or conductive carbon materials. Silver is an example of a preferred element to fabricate the nanostructured sensors since it is relatively low cost compared to gold, facile to use, and possesses a plasmonic quality factor that is several fold greater than gold. Nanopillars, grids, and other nanostructures can be formed, for example, by assembly of nanoparticles into the required form, with or without fusion of the nanoparticles into a solid mass.

There are several challenges that can be overcome by the technology. One example is the presence of moisture in the atmosphere that could mask the signal. The absorbance peak of methane at ~1650 nm coincides with the shoulder of a broad water absorbance band. Thus, a change in signal measured by the device could be due to a change of humidity instead of a change in methane concentration. This problem can be circumvented by including a second sensor that is tuned to absorb at the peak frequency of the water band, allowing for any changes in moisture content to be monitored. The signals from the two sensors can be compared and the differential taken as the true signal. This method can also compensate for any effects of temperature on the signal. Other hydrocarbons with diverse molecular structures can be detected by tuning sensors for NIR specificity.

The technology described herein can provide gas sensors that are compact, effective, robust, and relatively low cost compared to other sensors on the market. The sensor architecture can take advantage of the optical properties of nanomaterials to absorb light within a narrow band of the NIR spectrum that coincides with the absorbance of the desired gas. The sensor can be integrated into a package that can detect gas concentration and transmit the data to a nearby network. Through experiment and modeling, an optimum sensor geometry and minimum sensor area needed for a useable signal can be determined, allowing for the fabrication of optimized sensors.

REFERENCES

[1] A. Heinzel, V. Boerner, A. Gombert, V. Wittwer, and J. Luther, in *AIP Conf. Proc.* (American Institute of Physics, 1999), pp. 191-196.
[2] S. Maruyama, T. Kashiwa, H. Yugami, and M. Esashi, Appl. Phys. Lett. 79, 1393 (2001).
[3] H. Sai, Y. Kanamori, and H. Yugami, Appl. Phys. Lett. 82, 1685 (2003).
[4] T. Yokoyama, T. D. Dao, K. Chen, S. Ishii, R. P. Sugavaneshwar, M. Kitajima, and T. Nagao, Adv. Opt. Mater. 4, 1987 (2016).
[5] S. Tsuda, M. Shimizu, F. Iguchi, and H. Yugami, IEEE Trans. Components, Packag. Manuf. Technol. 5, 971 (2015).
[6] P. Senanayake, C.-H. Hung, J. Shapiro, A. Lin, B. Liang, B. S. Williams, and D. L. Huffaker, (1100) 2011.
[7] P. Senanayake, A. Lin, G. Mariani, J. Shapiro, C. Tu, A. C. Scofield, P. S. Wong, B. Liang, and D. L. Huffaker, Appl. Phys. Lett. 97, (2010).
[8] H. Nesser, J. Grisolia, A. Mlayah, T. Alnasser, D. Lagarde, B. Viallet, and L. Ressier, Mater. Today Nano 4, 38 (2018).
[9] A. E. cetin, A. A. Yanik, C. Yilmaz, S. Somu, A. Busnaina, and H. Altug, Appl. Phys. Lett. 98, 111110 (2011).
[10] C. Yilmaz, A. E. Cetin, G. Goutzamanidis, J. Huang, S. Somu, H. Altug, D. Wei, and A. Busnaina, ACS Nano 8, 4547 (2014).

What is claimed is:

1. A sensor device for gas detection; the device comprising:
    a housing configured with a flow path for a sample gas through the housing;
    a light source disposed within the housing to direct light across the flow path, the light source emitting light comprising an emission wavelength band overlapping with an absorbance spectrum or portion thereof of a first analyte selected for detection;
    a sensing element disposed within the housing to receive light emitted by the light source and crossing the flow path or a portion thereof, the sensing element comprising a nanostructure array of conductive nanoelements attached to a substrate and encapsulated in a dielectric material, wherein the nanostructure array and the dielectric material are tuned to provide plasmonic absorption by the conductive nanoelements over an absorbance wavelength band that overlaps with the absorbance spectrum or a portion thereof of the first analyte, such that a local field established by plasmonic modes of the nanostructure array affects a capacitance or inductance of the sensor device.

2. The device of claim 1, wherein the sensing element comprises a capacitive element, and the nanostructure array encapsulated in the dielectric material is disposed between opposed conductive surfaces of the capacitive element.

3. The device of claim 1, wherein the nanostructure array comprises nanoscale pillars, rods, or tubes having a spherical or polyhedral cross-sectional shape.

4. The device of claim 1, wherein the sensing element is connected with an electronic circuit capable of producing a signal in response to a change in capacitance or inductance of the sensing element.

5. The device of claim 1, further comprising a second sensor element tuned to detect a presence of a second analyte selected for detection, the second analyte having an absorbance wavelength band different from that of the first analyte.

6. The device of claim 1, wherein the light source emits light over an emission wavelength band in the range from about 700 nm to about 2500 nm.

7. The device of claim 1, wherein the dielectric material comprises polyethylene, polypropylene, polytetrafluoroethylene, polyethylene terephthalate, polycarbonate, poly(methyl methacrylate), polystyrene, polyimide, bisbenzocyclobutene resin, polyvinylidene chloride, titanium dioxide, strontium titanate, barium strontium titanate, barium titanate, calcium copper titanate, or a combination thereof.

8. The device of claim 1, wherein the nanostructure array comprises nanostructures with a height of about 400 nm.

9. The device of claim 1, wherein the nanostructure array comprises nanostructures with a diameter in the range from about 100 nm to about 250 nm.

10. The device of claim 1, wherein the nanostructure array comprises a plurality of periodically arranged apertures with a diameter of about 1 µm and a wall between adjacent apertures having a thickness of about 200 nm.

11. The device of claim 1, wherein the nanostructure array comprises nanostructures comprising silver, gold, platinum, copper, or a combination thereof.

12. A method of detecting a presence of a first selected analyte, the method comprising the steps of:
(a) providing the sensor device of claim 1;
(b) establishing a baseline capacitance or inductance when no analyte is present in the flow path;
(c) detecting a change in the capacitance or inductance when the first selected analyte is present in the flow path; and
(d) transmitting a signal representative of the change in the capacitance or inductance to electronic circuitry and/or a processor.

13. The method of claim 12, wherein the first selected analyte is selected from the group consisting of hydrogen, ammonia, hydrogen sulfide, hydrogen fluoride, and hydrocarbons.

14. The method of claim 12, wherein the first selected analyte is a hydrocarbon selected from the group consisting of methane, ethane, propane, and butane.

15. The method of claim 12, further comprising the steps of:
(c1) providing a second sensor element tuned to absorb at an absorbance wavelength band of a second analyte for detection;
(c2) detecting a change in capacitance or inductance when the second analyte is present in the flow path; and
(c3) transmitting a signal representative of the change in the capacitance or inductance to electronic circuitry or a processor.

16. The method of claim 15, wherein the first analyte is a hydrocarbon and the second analyte is a hydrocarbon different from the first analyte.

17. The method of claim 15, wherein the second analyte is water vapor.

18. A system for gas detection; the system comprising:
the sensor device of claim 1;
a pump and/or an inlet operative to transport a gas sample suspected of comprising the first analyte through the flow path; and
a processor operative to detect a change in capacitance or inductance of the sensor element when the first analyte is present in the flow path and to transmit information indicative of detection of the first analyte to a receiver or over a network.

19. The system of claim 18 comprising two or more sensor devices of claim 1, each of the two or more sensor devices operative to detect a different analyte present in the flow path.

20. The system of claim 19 configured to detect methane and a different hydrocarbon or methane and water vapor.

21. The system of claim 18, further comprising a mass flow meter operative to provide a measured flow of the sample analyte to the processor.

22. The system of claim 18 that is configured for deployment in an oil or gas rig, refinery, analytical lab, manufacturing facility, public transport area, flammable liquid or gas cylinder storage or distribution facility, vehicle, outdoor hazmat area, hazardous materials area, or residence.

* * * * *